US012758301B2

(12) United States Patent
Tachikawa et al.

(10) Patent No.: US 12,758,301 B2
(45) Date of Patent: Oct. 13, 2026

(54) ELECTRODE FOR HIGH-FREQUENCY MEDICAL DEVICE AND MEDICAL DEVICE

(71) Applicant: OLYMPUS CORPORATION, Tokyo (JP)

(72) Inventors: Asuka Tachikawa, Iruma (JP); Hiroaki Kasai, Akishima (JP); Yoshiyuki Ogawa, Machida (JP); Issei Maeda, Sagamihara (JP)

(73) Assignee: OLYMPUS CORPORATION, Tokyo (JP)

(*) Notice: Subject to any disclaimer, the term of this patent is extended or adjusted under 35 U.S.C. 154(b) by 283 days.

(21) Appl. No.: 18/372,388

(22) Filed: Sep. 25, 2023

(65) Prior Publication Data

US 2024/0016537 A1 Jan. 18, 2024

Related U.S. Application Data

(63) Continuation of application No. PCT/JP2021/026079, filed on Jul. 12, 2021.

(51) Int. Cl.
*A61B 18/14* (2006.01)
*A61B 18/00* (2006.01)

(52) U.S. Cl.
CPC .. *A61B 18/1445* (2013.01); *A61B 2018/0013* (2013.01); *A61B 2018/00404* (2013.01);
(Continued)

(58) Field of Classification Search
CPC .... C08G 59/066; C08G 59/226; C08G 59/50; C08G 59/62; C09D 163/00; C09D 5/4434; A61B 18/1445; A61B 2018/00077; A61B 2018/00107; A61B 2018/00125; A61B 2018/0013; A61B 2018/00136; A61B 2018/00148; A61B 2018/00404; A61B 2018/00589; A61B 2018/00595; A61B 2018/0063
See application file for complete search history.

(56) References Cited

U.S. PATENT DOCUMENTS

2017/0158935 A1 6/2017 Koh et al.
2018/0353658 A1 12/2018 Murano et al.
(Continued)

FOREIGN PATENT DOCUMENTS

JP 2017-148479 A 8/2017
JP 2018-075303 A 5/2018
(Continued)

OTHER PUBLICATIONS

International Search Report dated Sep. 28, 2021 received in PCT/JP2021/026079.

*Primary Examiner* — Tigist S Demie
(74) *Attorney, Agent, or Firm* — Scully, Scott, Murphy & Presser, P.C.

(57) ABSTRACT

An electrode for a high-frequency medical device in which a coating film is formed on at least a part of a surface of a treatment section of the medical device, wherein the coating film includes a silicone resin, and at least one type of filler having conductivity. Particles of the fillers are fusion-bonded to each other to form a conductive path, and/or a particle of the filler and an electrode substrate disposed on a surface of the treatment section are fusion-bonded to form a conductive path.

6 Claims, 11 Drawing Sheets

(52) U.S. Cl.
CPC ............... *A61B 2018/00589* (2013.01); *A61B 2018/00595* (2013.01); *A61B 2018/0063* (2013.01)

(56) References Cited

U.S. PATENT DOCUMENTS

| | | | | |
|---|---|---|---|---|
| 2019/0059994 | A1 | 2/2019 | Shin et al. | |
| 2019/0090934 | A1 | 3/2019 | Robinson et al. | |
| 2019/0192212 | A1 | 6/2019 | Murano et al. | |
| 2020/0164115 | A1 | 5/2020 | Murano et al. | |
| 2020/0205880 | A1* | 7/2020 | Kasai ................. | A61B 18/1402 |

FOREIGN PATENT DOCUMENTS

| | | | |
|---|---|---|---|
| JP | 2019-506211 | A | 3/2019 |
| JP | 2019-076218 | A | 5/2019 |
| JP | 2019-076494 | A | 5/2019 |

* cited by examiner

FIG. 10A

| | Example 1 | Example 2 | Example 3 | Example 4 | Example 5 |
|---|---|---|---|---|---|
| Filler (1) | — | — | a | b | c |
| Material | Silver | Silver | Silver | Alumina coated with silver | Silver |
| Shape | Flake shape with corners | Flake shape with corners | Flake shape with corners | Flake shape with corners | Flake shape with corners |
| Average particle size μm | 2 | 3.5 | 3.5 | 13 | 3.5 |
| True density g/cm$^3$ | 10.5 | 12.0 | 10.5 | 5.8 | 10.5 |
| Filler (2) | None | None | None | None | e |
| Material | — | — | — | — | Silver |
| Shape | — | — | — | — | Small particle size and high density |
| Average particle size μm | — | — | — | — | 0.8 |
| True density g/cm$^3$ | — | — | — | — | 10.5 |
| Added amount wt% | 90 | 90 | 80 | 60 | 50<br>10 |
| Curing temperature °C | 150 | 150 | 150 | 200 | 180 |
| Conductivity | A | A | A | A | A |
| Adhesion | A 35 times | A 40 times | A 32 times | A 36 times | AA 63 times |

FIG. 10B

| | Comparative Example 1 | Comparative Example 2 | Comparative Example 3 | Comparative Example 4 | Comparative Example 5 | Comparative Example 6 |
|---|---|---|---|---|---|---|
| Filler (1) | a | a | c | d | e | f |
| Material | Silver | Silver | Copper coated with silver | Alumina coated with silver | Silver | Carbon |
| Shape | Flake shape with corners | Flake shape with corners | Flake shape without corners | Spherical | Small particle size and high density | Fine carbon particles |
| Average particle size μm | 3.5 | 3.5 | 6.5 | 7.0 | 0.8 | 0.04 |
| True density g/cm$^3$ | 10.5 | 10.5 | 9.2 | 3.5 | 10.5 | Unknown |
| Filler (2) | None | None | None | None | None | None |
| Material | — | — | — | — | — | — |
| Shape | — | — | — | — | — | — |
| Average particle size μm | — | — | — | — | — | — |
| True density g/cm$^3$ | — | — | — | — | — | — |
| Added amount wt% | 80 | 95 | 88 | 73 | 96 | 17 |
| Curing temperature °C | 140 | 140 | 200 | 200 | 150 | 150 |
| Conductivity | B | A | A | A | A | B |
| Adhesion | Evaluation not possible | B peeled off after 5 times or less | B peeled off after 5 times or less | B peeled off after 5 times or less | B peeled off after 5 times or less | B peeled off after 5 times or less |

ELECTRODE FOR HIGH-FREQUENCY MEDICAL DEVICE AND MEDICAL DEVICE

CROSS-REFERENCE TO RELATED APPLICATIONS

The present application is a continuation application based on PCT Patent Application No. PCT/JP2021/026079, filed on Jul. 12, 2021, the entire content of which is hereby incorporated by reference.

BACKGROUND

Technical Field

The present invention relates to an electrode for a high-frequency medical device and a medical device.

Description of the Background

Devices that apply a high-frequency voltage to living tissue are known as medical devices. For example, a high-frequency surgical instrument, which is an example of such a medical device, cuts, coagulates, or cauterizes living tissue by applying a high-frequency voltage to the living tissue.

In such a medical device, in order to satisfy the function of treating living tissue, the portion of the surface that comes into contact with living tissue needs to be conductive. However, metals with good conductivity tend to adhere to living tissue, and the visibility and operability during use of the high-frequency treatment instrument may deteriorate.

For example, U.S. Patent Publication No. 2019/0090934 (hereinafter referred to as Patent Document 1) describes an electrode that prevents deterioration of visibility and operability during use by preventing living tissue from adhering to a conductive portion. Patent Document 1 describes an electrode in which the surface of a conductive portion is coated with a thin film of polydimethylsiloxane as a technique for preventing adhesion of living tissue.

However, the above conventional technology has a following problem.

According to the technology described in Patent Document 1, polydimethylsiloxane, which is the thin film that constitutes the electrode, has methyl groups in the side chains, so it is difficult to form hydrogen bonds with the electrode substrate and is easily separated. In other words, the biological tissue sticks to the peeled portion of the thin film, and the anti-sticking property of preventing the adhesion of the biological tissue deteriorates due to repeated use.

Here, in order to secure conductivity in a thin film for providing sticking prevention properties as a high-frequency electrode, a technique of mixing a conductive filler with a silicone resin is known. Also, the silicone resin is responsible for ensuring sticking prevention properties and adhesion to the electrode substrate. In this case, in order to ensure sufficient conductivity, it is necessary to increase the ratio of the conductive filler to the silicone resin. However, if the proportion of the conductive filler is increased too much, the sticking prevention performance is lowered and the adhesion to the electrode substrate is also lowered, resulting in peeling.

Therefore, even if the amount of conductive filler is reduced, there is a demand for a high-frequency electrode made of a thin film that has sufficient conductivity and anti-sticking properties.

SUMMARY

The present invention provides an electrode for a high-frequency medical device and a medical device, which maintains good conductivity without reducing sticking prevention performance, and which makes it difficult for living tissue to adhere even when repeatedly used for treatment of living tissue.

A first aspect of the present invention provides an electrode for a high-frequency medical device in which a coating film is formed on at least a part of a surface of a treatment section of the medical device. The coating film includes a silicone resin, and at least one type of filler having conductivity. Particles of the filler are fusion-bonded to each other to form a conductive path, and/or a particle of the filler and the electrode substrate disposed on a surface of the treatment section are fusion-bonded to form a conductive path.

In the electrode for a high-frequency medical device, the filler preferably has a shape having corners.

In the electrode for a high-frequency medical device, the filler may have an average particle diameter of 3 μm or more, which is smaller than the film thickness of the coating film, and may have a true density of 11 $g/cm^3$ or less.

In the electrode for a high-frequency medical device, the filler may have a configuration in which a core composed of aluminum, copper, a ceramic such as alumina, silica, glass, and calcium titanate fiber, a resin such as acryl, a hollow particle, and rubber is coated with material with volume resistance ratio of 9 ohm or less, such as silver or gold.

In the electrode for a high-frequency medical device, the filler may be composed of two or more types of fillers having different particle sizes, and a filler having a small particle size may have a higher ratio in the vicinity of the electrode substrate.

A medical device according to a second aspect of the present invention includes the electrode for a high-frequency medical device described above.

According to the electrode for a high-frequency medical device and the medical device of the present invention, good conductivity can be maintained without deteriorating sticking prevention performance, which makes it difficult for living tissue to adhere even when repeatedly used for treatment of living tissue.

BRIEF DESCRIPTION OF THE DRAWINGS

FIGS. 10A and 10B contain Tables 1 and 2, respectively, that show schematic configurations and evaluation results of each example and comparative example.

DETAILED DESCRIPTION

Embodiments

Electrodes for high-frequency medical devices and medical devices according to embodiments of the present invention will be described below with reference to the drawings.

Figure 1:
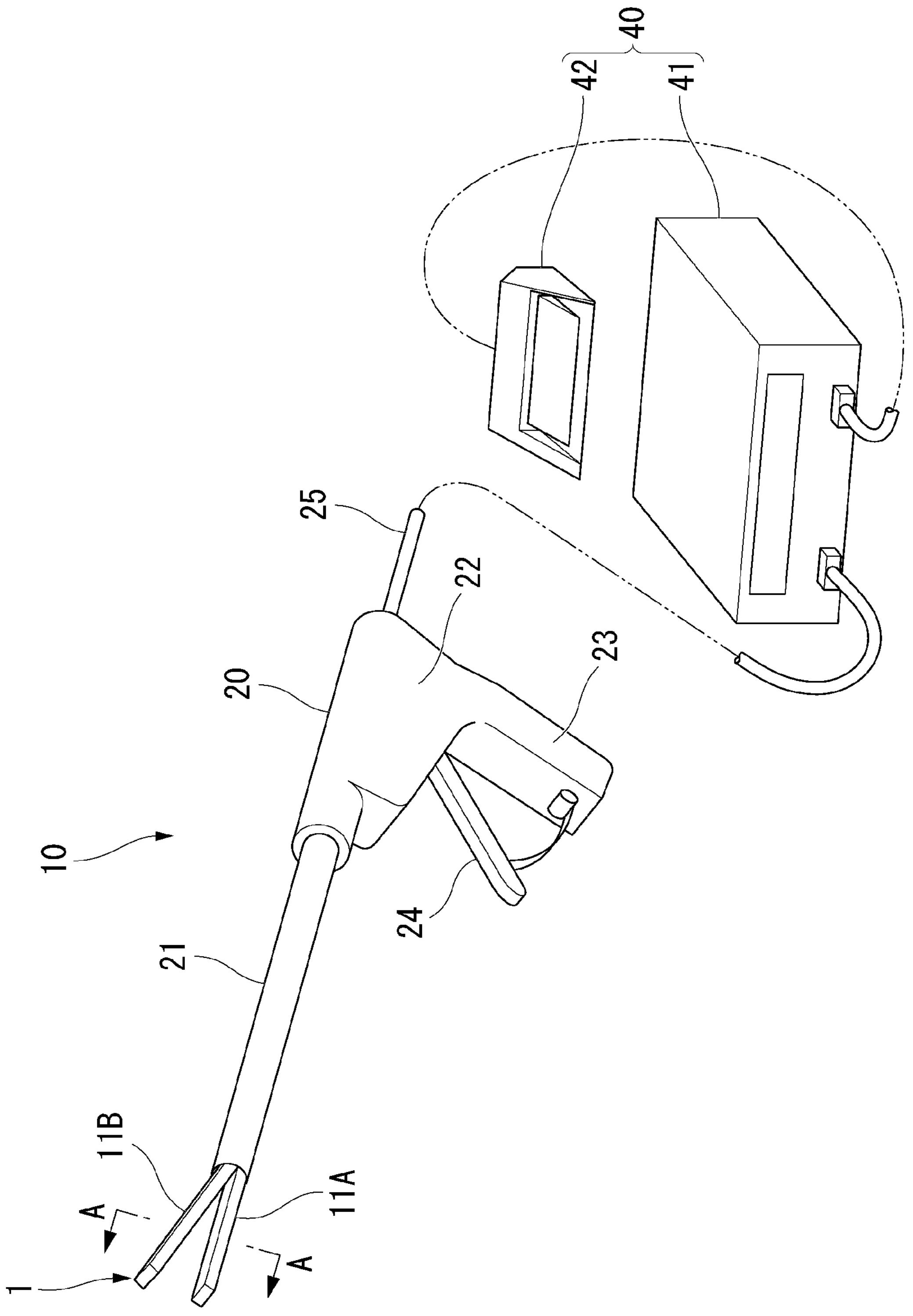
FIG. 1 is a schematic configuration diagram showing an example of a medical device according to an embodiment of the present invention.
Figure 2:
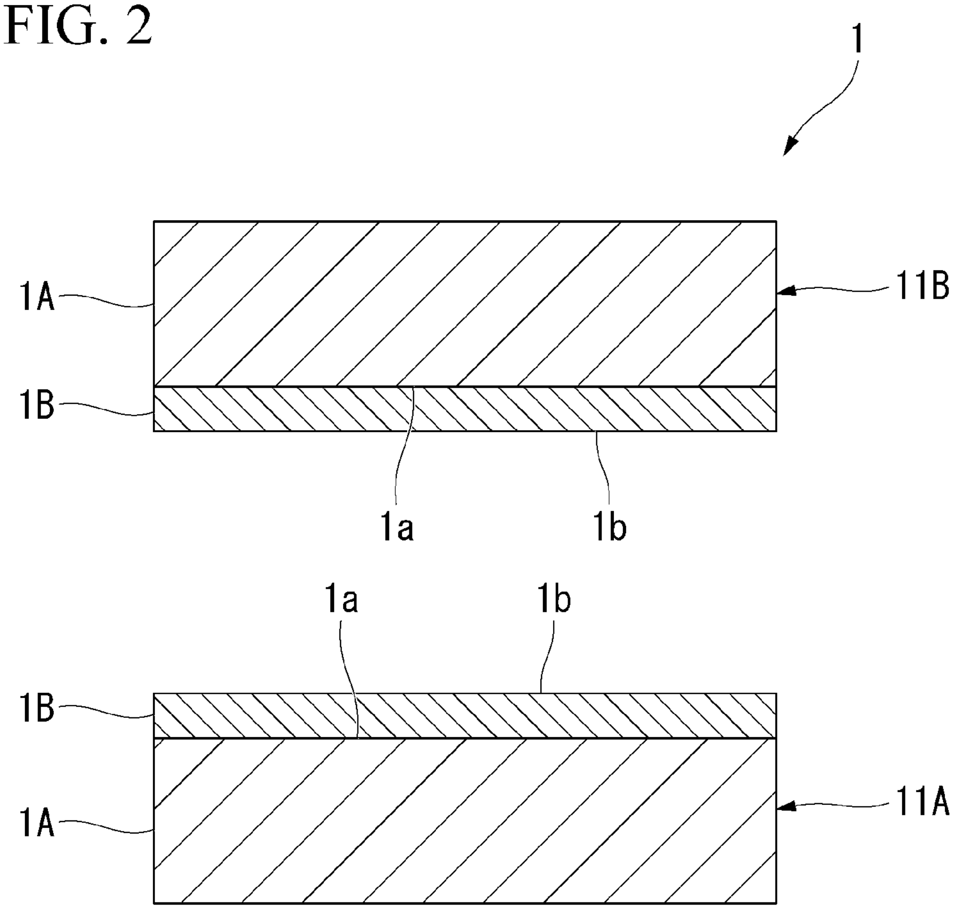
FIG. 2 is a cross-sectional view taken along line A-A in FIG. 1.
Figure 3:
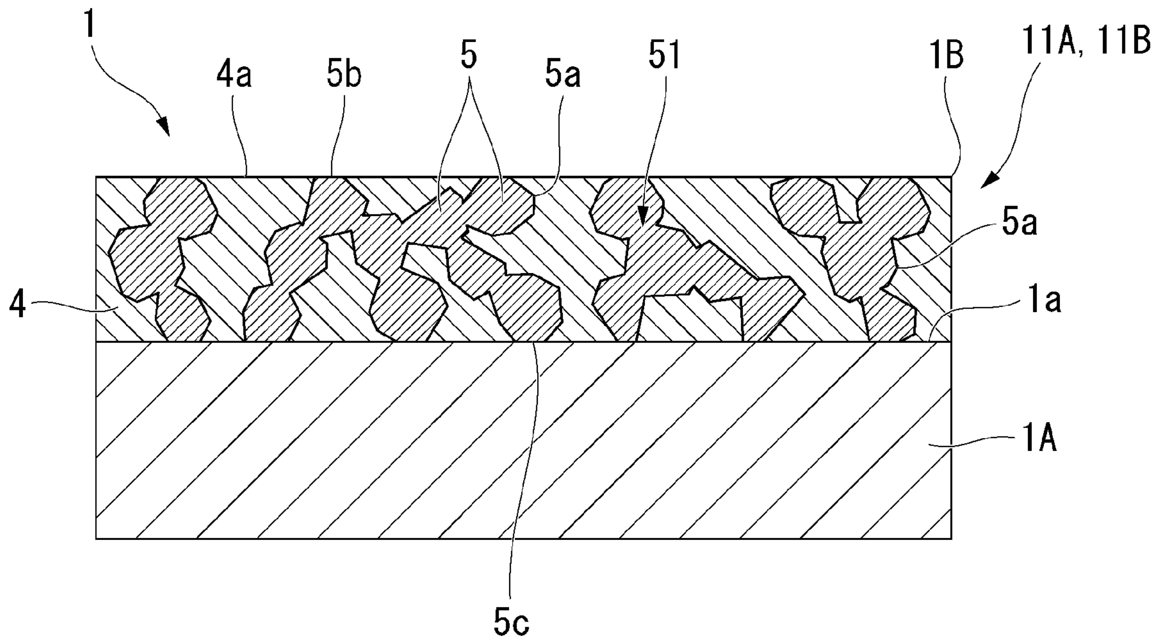
FIG. 3 is a schematic cross-sectional view of an electrode for a high-frequency medical device according to an embodiment of the present invention.

FIG. 1 is a schematic configuration diagram showing an example of a medical device according to an embodiment of the present invention. FIG. 2 is a cross-sectional view taken along line A-A in FIG. 1. FIG. 3 is a schematic cross-sectional view of an electrode for a high-frequency medical device according to an embodiment of the present invention.

Because each drawing is a schematic diagram, the shape and dimensions are exaggerated (the same applies to the following drawings).

A high-frequency device 10 of this embodiment shown in FIG. 1 is an example of the medical device of this embodiment. The high-frequency device 10 is a bipolar medical treatment instrument that coagulates (stops bleeding) or cauterizes living tissue by applying a high-frequency voltage between opposing electrodes.

The high-frequency device 10 includes a handle-shaped operating portion 20 for an operator to hold by hand, an electrode portion 1 provided at the distal end of a shaft 21 protruding from the distal end of the operating portion 20, and a power supply unit 40 electrically connected to the electrode portion 1 via the operating portion 20

The electrode portion 1 is provided with a pair of electrode portions 11A and 11B. A second electrode portion (here, numeral 11B) is provided so as to be capable of opening and closing with respect to a first electrode portion (here, numeral 11A). The first electrode portion 11A is a fixed electrode, and the second electrode portion 11B is a movable substrate.

The operating portion 20 includes an operating portion main body 22, a grip portion 23, and an operating handle 24. Inside the operating portion main body 22, the operating handle 24 is connected to a wire or rod inserted through the shaft 21 and the wire or rod is connected to the second electrode portion 11B. Displacement of the operating handle 24 based on the operator's operation is transmitted to the second electrode portion 11B through the wire or rod to which the operating handle 24 is connected. Thereby, the second electrode portion 11B is displaced with respect to the first electrode portion 11A in accordance with the movement of the operating handle 24.

One end of a cable 25 extending from the power supply unit 40 is connected to the proximal end side of the operating portion 20. The other end of cable 25 is connected to the power supply unit 40. An electrical signal line for applying high-frequency power to the pair of electrode portions 11A and 11B are inserted through the cable 25.

The power supply unit 40 includes a control portion 41 and a high-frequency driving portion 42.

The control portion 41 controls each part of the high-frequency device 10. For example, the control portion 41 controls the operation of the high-frequency driving portion 42 according to the operation input from the operating handle 24.

The high-frequency driving portion 42 supplies high-frequency current to the electrode portion 1 according to the control signal sent from the control portion 41. The high-frequency power is applied to the electrode portion 1 constituting the bipolar electrode through an electric signal line (not shown) inserted through the cable 25.

The electrode portion 1 applies a high-frequency voltage while gripping a biological tissue (for example, a blood vessel) that is an object to be treated. The outer shape of each of the first electrode portion 11A and the second electrode portion 11B that constitute the electrode portion 1 is, as a whole, a linear or curved rod-like or plate-like shape.

As shown in FIG. 2, the pair of electrode portions 11A and 11B each include a metal electrode substrate 1A and a conductive adhesion preventing film 1B (coating film) of the present embodiment. The conductive adhesion preventing film 1B is coated on a surface of the electrode substrate 1A, which surface is facing to the other electrode portion.

As the material of the electrode substrate 1A, an appropriate conductive metal material such as a metal or an alloy is used. For example, an aluminum alloy, stainless steel, copper, or the like may be used as the material of the electrode substrate 1A.

As shown in FIG. 2, the conductive adhesion preventing film 1B is a film provided so as to cover the electrode substrate surface 1*a*. The outer surface of the conductive adhesion preventing film 1B constitutes the electrode surface 1*b* of the electrode portion 1.

As schematically shown in FIG. 3, the conductive adhesion preventing film 1B includes a silicone resin 4 as a base material and one type of conductive filler 5 dispersed in the silicone resin 4. In the conductive adhesion preventing film 1B, particles of the filler 5 are combined each other by thermal fusion and/or a particle of the filler 5 and the electrode substrate 1A located on the surface of the treatment area are combined by thermal fusion. The thermal fusions are made at points or on surface areas of the particle.

That is, in the manufacturing process, external energy is applied to the conductive adhesion preventing film 1B containing the filler 5 to heat the filler 5 and soften or melt at least a portion of the filler 5, thereby making the filler 5 deformable. This deformable particle of the filler 5 is combined to other particle of the filler 5 at a point or on surface area, or combined to the electrode substrate 1A at a point or on surface area. Combining on the surface is a concept that includes integration by fusion. This point or surface combining by fusion is maintained even after the filler 5 cools and hardens. This point or surface combining by fusion is hereinafter referred to as fusion combining. A portion of the filler 5 (exposed portion 5*b*) is exposed from the silicone resin 4 to the outside. The surface 4*a* of the silicone resin 4 and the exposed portion 5*b* of the filler 5 exposed from the surface 4*a* of the silicone resin 4 constitute the electrode surface 1*b*. A portion of the filler 5 (combined portion 5*c*) is combined to the electrode substrate 1A by fusion bonding. When the filler 5 is not exposed and the film thickness between the filler 5 and the surface 4*a* of the silicone resin 4 is 1 μm or less, the adhesion prevention property is further improved. Moreover, when the film thickness is 100 nm or less, the treatment performance is further enhanced.

The film thickness of the conductive adhesion preventing film 1B can be set to an appropriate thickness with which the required strength for the high-frequency device can be obtained. For example, the film thickness of the conductive adhesion preventing film 1B may be about 5 μm.

As the silicone resin 4, a non-conductive material that does not easily adhere to living tissue and has heat resistance that can withstand the heat generated when the high-frequency device 10 is used, can be used. The silicone resin 4 may have a lower thermal conductivity than the filler 5 described later. In this case, the silicone resin 4 also has excellent heat insulation performance.

Figure 4:
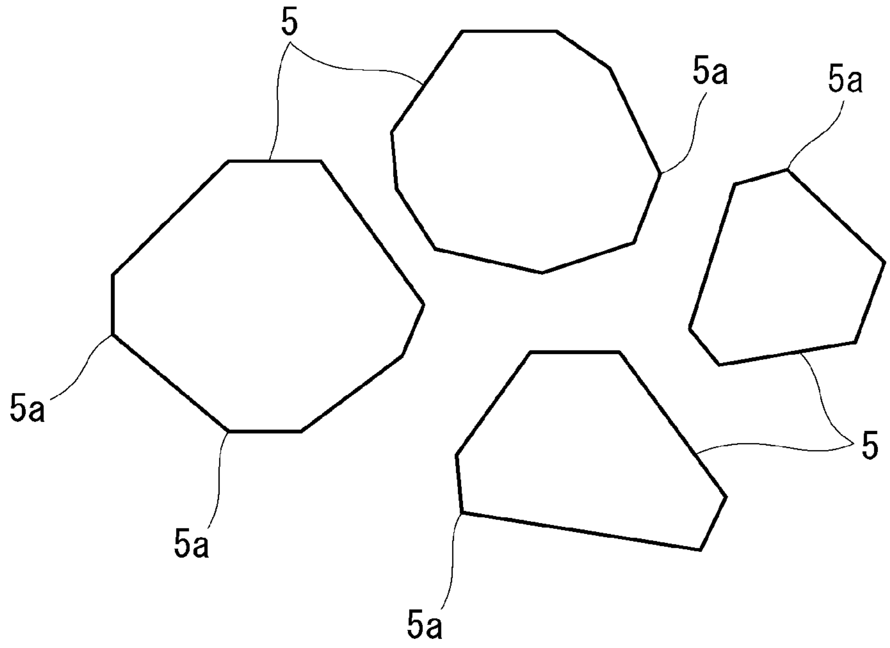
FIG. 4 is a schematic diagram showing the structure of a conductive filler of an electrode for a high-frequency medical device.

FIG. 3 is a schematic diagram in which individual particles of the filler 5 are fused to each other at the fused portion 51. One filler 5 is formed in a flake shape having at least one corner 5*a*, as shown in FIG. 4. More preferably, the filler 5 has an average particle diameter of 3 μm or more, which is smaller than the film thickness of the conductive adhesion preventing film 1B (for example, about 5 μm as described above), and a true density of 11 g/cm$^3$ or less. The filler 5 may have a substantially polygonal shape with a chamfered apex as in the example of FIG. 4, or may have a substantially rectangular elongated shape as shown in a first modified example described later. For the filler 5 having such a shape, the length of the maximum diameter should satisfy the above numerical range of the average particle size. The corners 5*a* of particles of the fillers 5 are easily melted by heat, and are easily fused to other adjacent particles of the filler 5.

The average particle diameter and true density of the filler 5 are measured by processing the cross section of the conductive adhesion preventing film 1B and observing the filler 5 on the processed surface with an electron microscope. Ion milling processing may be used as the cross-sectional processing.

When the shape of the fillers 5 is flake-like without corners or spherical, the fillers 5 are not thermally fused well to each other due to the lack of melting of the corners. Therefore, it becomes difficult to form a conductive path, and sufficient conductivity cannot be obtained.

The material of the filler 5 may be metal. The electrical resistivity of the metal used for the filler 5 may be, for example, 952 or less. Examples of metals with low electrical resistivity include silver, nickel, copper, and gold. In particular, nickel and copper are more preferable because they are cheaper than silver, gold, and the like. However, the filler 5 is not limited to metal as long as it has electrical conductivity.

For example, as the filler 5, a composite material in which a core made of aluminum, copper, alumina, silica, glass, ceramics such as calcium titanate fibers, resins such as acrylic, hollow particles, rubber, or the like is coated with a conductive metal such as silver may be used. In this case, the metal more preferably covers the entire surface of the non-conductive material. The point is that the coating material should be capable of fusing particles of the filler 5 together by heat.

Examples of non-conductive materials include inorganic materials such as glass, silica, alumina, and zirconia. As the material of the non-conductive substance in the composite material, a resin material having heat resistance that can withstand heat generated when the high-frequency device 10 is used, may be used.

The non-conductive substance may have a hollow structure. When the non-conductive substance has a hollow structure, the heat insulating properties of the filler 5 can be improved.

Examples of metals in the composite material include silver, nickel, copper, and gold. Methods such as electroless plating, PVD (Physical Vapor Deposition), and CVD (Chemical Vapor Deposition) are applicable as coating methods for coating these metals on the surface of the core. Examples of PVD include, for example, sputtering, vapor deposition, and the like.

When the filler 5 is formed of a composite material of a non-conductive substance and a metal, the amount of expensive metal used is reduced compared to the filler 5 of all metal. Therefore, the cost of parts of the filler 5 is reduced.

For example, a nonmetallic conductor may be used as the filler 5. Carbon fibers, carbon nanotubes, and the like may be used as the non-metallic conductor.

The amount of the filler 5 added to the conductive adhesion preventing film 1B is preferably in the range of 60 wt % to 90 wt %, for example.

If the amount of the filler 5 added is less than 60 wt %, the probability of particles of the filler 5 being fused to each other within the conductive adhesion preventing film 1B decreases, so the continuity due to the fusion of particles of the filler 5 to each other reduced, and the conductive paths are lessened. In this case, good conductivity cannot be obtained in the conductive adhesion preventing film 1B.

When the added amount of the filler 5 exceeds 90 wt %, the area of the filler 5 exposed on the electrode surface 1*b* becomes too large, and the interval between the exposed portions 5*b* becomes too narrow. As a result, on the electrode surface 1*b*, the surface area of the silicone resin 4, which has a high ability to prevent adhesion of living tissue, is reduced, so that the ability to prevent adhesion of living tissue on the electrode surface 1*b* deteriorates.

The average particle size of the filler 5 is preferably 2 μm or more. If the length of the filler 5 is less than 2 μm, the probability that one particle of the filler 5 will fuse with another particle of the filler 5 in the longitudinal direction decreases. In this case, good conductivity cannot be obtained in the conductive adhesion preventing film 1B.

The conductive adhesion preventing film 1B having the configuration described above may be formed by coating, for example. In this case, first, a paint is produced in which the silicone resin 4 and the filler 5 are dispersed in an appropriate dispersion liquid such as water. After that, this paint is applied to the electrode substrate surface 1*a* of the electrode substrate 1A by a suitable coating means. The coating means is not particularly limited.

Examples of coating means include spray coating, dip coating, spin coating, screen printing, inkjet method, flexographic printing, gravure printing, pad printing, and hot stamping. Spray coating and dip coating are particularly suitable as coating means for forming the conductive adhesion preventing film 1B on the medical device because they can be easily coated even if the shape of the object to be coated is complicated.

When the paint is applied to the electrode substrate surface 1*a* of the electrode substrate 1A, the filler 5 moves within the paint until the paint dries. At this time, the filler 5 in the paint is oriented along the electrode substrate surface 1*a*, which is the coated surface, by an external force acting from the coating means during coating, gravity, or the like. That is, a particle of the filler 5 in the paint is mixed with the silicone resin 4 and combined with other particles of the fillers 5, and tends to take a posture in parallel or at a shallow angle with the electrode substrate surface 1*a*.

After the coating film is formed on the electrode substrate surface 1*a*, the dispersion is evaporated by drying. As a result, the conductive adhesion preventing film 1B in which the filler 5 is dispersed in the silicone resin 4 is formed.

Next, the operation of the high-frequency device 10 having such a configuration will be described.

A treatment using the high-frequency device 10 is performed, for example, in a state in which a patient's affected area is held by the electrode portions 11A and 11B and a high-frequency voltage is applied to the electrode portions 11A and 11B by a high-frequency power supply 3.

The electrode portion 1 is covered with the conductive adhesion preventing film 1B. Particles of the filler 5 are dispersed inside the conductive adhesion preventing film 1B. Inside the conductive adhesion preventing film 1B, a large number of particles of the filler 5 are dispersed in a mutually fused state. Therefore, most of particles of the filler 5 are directly or indirectly connected to the electrode substrate surface 1*a*. That is, inside the conductive adhesion preventing film 1B, a large number of conductive paths are formed to connect the end portion (exposed portion 5*b*) of the filler 5 forming a part of the electrode surface 1*b* and the electrode substrate surface 1*a*, by particles of the filler 5 that are combined to each other by fusion.

The electrode surface 1*b* of the conductive adhesion preventing film 1B is a smooth surface made of the silicone resin 4 except for the filler 5 exposed from the silicone resin 4. The area of the exposed portion of the filler 5 in plan view is much smaller than the surface area of the silicone resin 4. The amount of protrusion of the exposed portion of the filler 5 from the surface of the silicone resin 4 is also very small.

When a high-frequency voltage is applied between the electrode portions 11A and 11B, a high-frequency current is generated through the conductive adhesion preventing film 1B. The conductive portion in the contact portion between the electrode surface 1*b* of the electrode portion 1 and the living tissue is the exposed portion of the filler 5, so the area is extremely small compared to the area of the electrode portion 1. Therefore, at the contact portion between the electrode portion 1 and the living tissue, a current with a high density flows from the filler 5 exposed on the electrode surface 1*b* to the living tissue, generating Joule heat. As a result, water in the living tissue of the object to be treated evaporates rapidly, and the living tissue is cauterized, thereby enabling hemostasis and coagulation.

When the necessary treatment is completed, the operator separates the electrode portion 1 from the treated body. At this time, most of the electrode surface 1*b* in contact with the living tissue is not the filler 5 to which the living tissue easily adheres, but the silicone resin 4 to which the living tissue hardly adheres. Therefore, when the electrode portion 1 is separated, the living tissue is easily separated from the electrode surface 1*b*.

The electrode surface 1*b* is a rough surface with minute protrusions formed by the exposed portions of the filler 5. For this reason, as compared with the case where the electrode surface 1*b* consists only of a smooth surface such as the surface of the silicone resin 4, electric discharge is more likely to occur from the protrusions and the treatment ability is enhanced, but the adhesion prevention property is lowered. A state in which the protrusions formed by the filler 5 are covered with a thin silicone resin film is ideal in terms of both treatment ability and adhesion prevention property.

Thus, in the high-frequency device 10, almost no living tissue adheres to the electrode surface 1*b*.

If a living tissue that cannot be completely peeled off adheres to the electrode surface 1*b*, the electrical conductivity of the adhered portion will be reduced, and electric energy will not be sufficiently emitted from the adhered portion. For this reason, the treatment performance is lowered at the attachment portion of the living tissue.

However, as described above, since living tissue hardly adheres to the electrode surface 1*b* of the electrode portion 1, the high-frequency device 10 can prevent treatment Furthermore, the durability of the performance from deteriorating during treatment electrode portion 1 is ensured even if the electrode portion 1 is used repeatedly.

In the present embodiment, the filler 5 in the conductive adhesion preventing film 1B has conductivity and corners 5*a*, particles of the filler 5 are bonded together, and the filler 5 and the electrode substrate 1A are bonded together. That is, the conductive adhesion preventing film 1B of the silicone resin 4 containing the filler 5 is formed on the surface of the electrode substrate 1A. Since the electrode substrate 1A is fused and a conductive path is formed by heating, the conductivity of the conductive adhesion preventing film 1B is improved. In this way, when particles of the filler 5 are fused to each other, the mutual bonding area increases and a thick conductive path is formed. Therefore, the amount of filler 5 added can be reduced, and sufficient conductivity can be obtained even with a small amount of filler 5 added.

As described above, in the conductive adhesion preventing film 1B of the present embodiment, by containing an appropriate amount of the filler 5 in the silicone resin 4, it is possible to achieve both the conductivity of the conductive adhesion preventing film 1B and the adhesion prevention property of the biological tissue.

In addition, in the embodiment, by setting the average particle size of the filler 5 to 3 μm or more and the true density to 11 g/cm 3 or less, the fusion bonding area of the filler 5 with the electrode substrate 1A can be increased, and good conductivity can be obtained.

In addition, since the filler 5 forms mesh-like bonds in the silicone resin 4, the silicone resin 4 can be held with high strength.

As described above, according to the high-frequency device 10 of the present embodiment, the conductive adhesion preventing film 1B is provided on the surface of the electrode portion 1. Therefore, even if the device is repeatedly used for treatment of living tissue, it is difficult for living tissue to adhere thereto, and the electrical conductivity can be maintained in good condition. Therefore, the high-frequency device 10 has excellent durability.

First Modified Example

An electrode for a high-frequency medical device and a medical device according to the first modified example of the present embodiment will be described.

Figure 5:
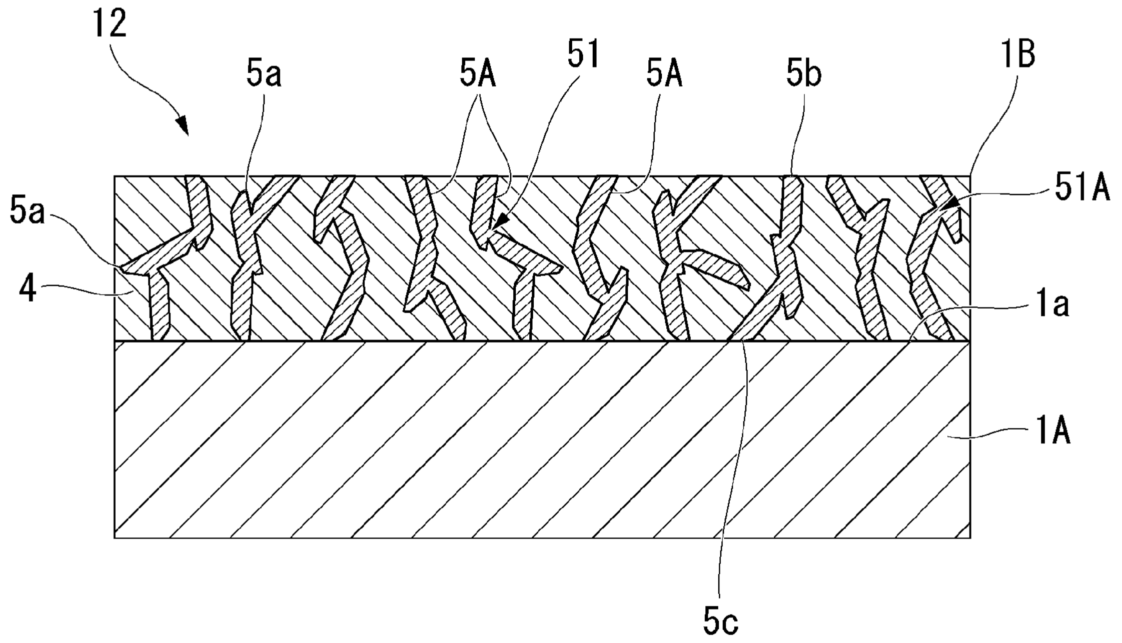
FIG. 5 is a schematic cross-sectional view of an electrode for a high-frequency medical device according to a first modified example of the embodiment of the present invention.

FIG. 5 is a schematic cross-sectional view of an electrode for a high-frequency medical device according to the first modified example of the embodiment of the present invention.

As shown in FIG. 1, a high-frequency device 10A (medical device) of the first modified example includes an electrode portion 12 instead of the electrode portion 1 in the above embodiment. As shown in FIG. 2, the electrode part 12 in the first modified example includes a conductive adhesion preventing film 1B (coating film) containing a filler 5A having a different shape from that of the above embodiment.

The following description will focus on points that differ from the above embodiment.

As schematically shown in FIG. 5, the conductive adhesion preventing film 1B has a silicone resin 4 similar to that of the above embodiment and a filler 5A having a different shape from that of the above embodiment. The filler 5A is formed in an elongated flake shape with corners 5*a*. As in the above embodiment, the filler 5A preferably has an average particle diameter of 3 μm or more in the longitudinal direction, which is smaller than the film thickness of the conductive adhesion preventing film 1B, and has a true density of 11 g/cm 3 or less. Also, in the conductive adhesion preventing film 1B of the first modified example, particles of the filler 5A are combined by thermal fusion and/or the filler 5A and the electrode substrate 1A located on the surface of the treatment section are combined by thermal fusion. The corner portions 5*a* of the filler 5A are easily melted by heat, and are easily fused to other adjacent fillers 5A.

In addition, in FIG. 5, the fused filler 5A is drawn so as to extend straight. However, the filler 5A is not limited to a straight shape as long as it can be well dispersed in the conductive adhesion preventing film 1B as in the above embodiment. The filler 5A may be curved or bent as long as it has a shape that allows it to be arranged within the range of the film thickness of the conductive adhesion preventing film 1B when dispersed in the conductive adhesion preventing film 1B.

Also, in the conductive adhesion preventing film 1B according to the first modified example, the amount of the filler 5A added is preferably in the range of 60 wt % to 90 wt %, for example, as in the above embodiment. Furthermore, the average particle size of the filler 5A is preferably 2 μm or more as in the above embodiment.

The material of the filler 5A is the same as in the above embodiment, and may be metal. The electrical resistivity of the metal used for the filler 5A may be, for example, 9Ω or less. Examples of metals with low electrical resistivity include silver, nickel, copper, and gold.

According to the high-frequency device 10A according to the first modified example, since the conductive adhesion preventing film 1B is provided on the surface of the electrode portion 11, even if the device is repeatedly used for treatment of the living tissue the living tissue does not adhere easily and the electrical conductivity can be maintained in good condition. Therefore, the high-frequency device 10A has excellent durability.

In particular, in the first modified example, since the filler 5A is elongated and has a shape with corners, even a small amount of the filler 5A is easily fused and a conductive path can be formed more reliably. That is, by setting the amount of the filler 5A added to, for example, about 60 wt %, the area of the filler 5A exposed on the electrode surface 1*b* can be reduced, and it is possible to prevent the gap between the exposed portions 5*b* of the filler 5A from becoming too narrow. As a result, on the electrode surface 1*b*, the surface area of the silicone resin 4 having high adhesion prevention property of the living tissue can be secured, and the adhesion prevention property of the living tissue on the electrode surface 1*b* can be maintained.

Second Modified Example

An electrode for a high-frequency medical device and a medical device according to a second modified example of the present embodiment will be described.

Figure 6:
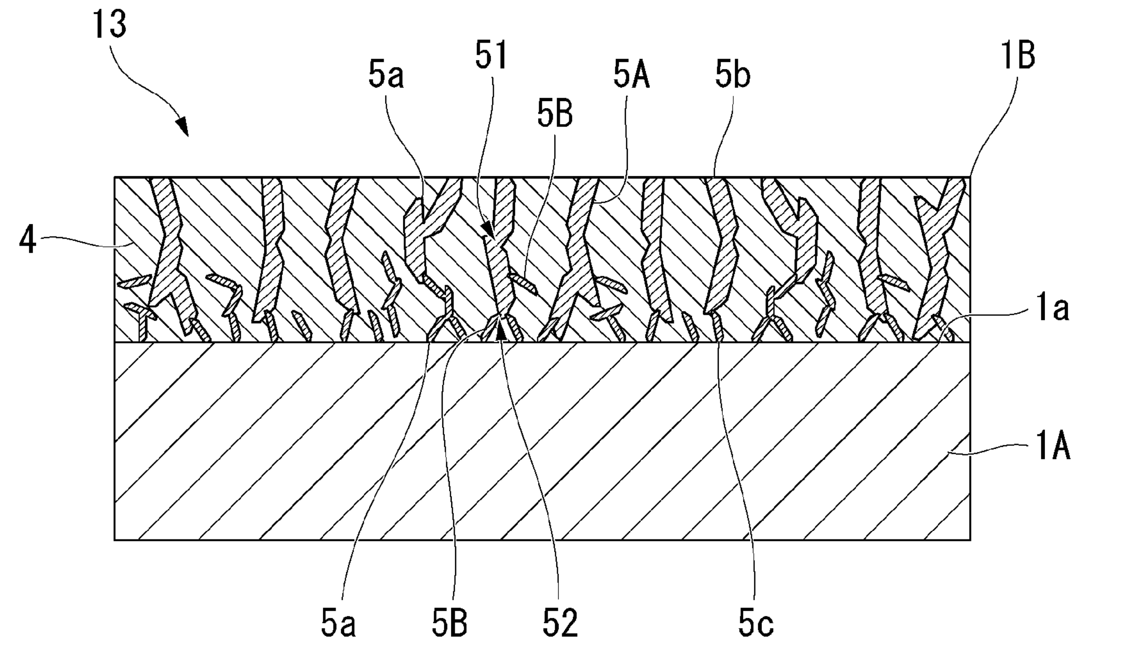
FIG. 6 is a schematic cross-sectional view of an electrode for a high-frequency medical device according to a second modified example of the embodiment of the present invention.

FIG. 6 is a schematic cross-sectional view of an electrode for a high-frequency medical device according to a second modified example of the embodiment of the present invention.

As shown in FIG. 1, a high-frequency device 10B (medical device) of the second modified example includes an electrode portion 13 instead of the electrode portion 12 of the first modified example. As shown in FIGS. 2 and 6, the electrode portion 13 in the second modified example includes the conductive adhesion preventing film 1B (medical conductive adhesion preventing film) containing fillers 5A and 5B of two different sizes.

The following description will focus on the differences from the second modified example.

As schematically shown in FIG. 6, the conductive adhesion preventing film 1B includes the filler 5A in the first modified example (referred to as large-diameter filler 5A in the second modified example) and the filler 5B having a smaller average particle size than the large-diameter filler 5A (referred to as small-diameter filler 5B in this second modified example). In the vicinity of the electrode substrate 1A, the ratio of the small-diameter filler 5B having a small particle diameter is higher.

Particles of the large-diameter filler 5A are mainly dispersed on the electrode surface 1*b* side of the conductive adhesion preventing film 1B, and are formed into elongated flake shapes having corners 5*a*. The large-diameter filler 5A is dispersed in the silicone resin 4 with an average particle diameter of 1 μm or more in the longitudinal direction, and more preferably 3 μm or more and a true density of 11 g/cm 3 or less.

Particles of the small-diameter fillers 5B are mainly dispersed on the electrode substrate surface 1*a* side of the conductive adhesion preventing film 1B, have a similar shape to the large-diameter filler 5A, and are formed into elongated flake shapes having corners 5*a*. The small-diameter filler 5B has an average particle diameter of less than 1 μm in the longitudinal direction and is smaller than the large-diameter filler 5A dispersed in the silicone resin 4. In particular, the small diameter filler 5B may be less than 0.5 μm.

Both the large-diameter filler 5A and the small-diameter filler 5B are partially melted and combined by fusion. Furthermore, the small-diameter filler 5B is also combined to the electrode substrate surface 1*a* of the electrode substrate 1A.

The boundary between the upper layer in which the large-diameter fillers 5A are mainly dispersed and the lower layer in which the small-diameter fillers 5B are mainly dispersed may be clear or unclear. That is, the large-diameter filler 5A may be dispersed in the lower layer, or the small-diameter filler 5B may be dispersed in the upper layer.

The large-diameter filler 5A and the small-diameter filler 5B may be solid or hollow, may be a single conductive substance, or may be a non-conductive core coated with a conductive substance. The small-diameter filler 5B is preferably solid and has a high density and a true density of 4.5 g/cm 3 or more. It is more preferable that the large-diameter filler 5A have a low density of 3 g/cm 3 or less, and a hollow density of 2 g/cm 3 or less.

Examples of the material of the non-conductive substance when the core in which the fillers 5A and 5B are non-conductive substances are coated with the conductive substance include inorganic materials such as glass, silica, alumina, and zirconia.

According to the high-frequency device 10B of the second modified example, since the conductive adhesion preventing film 1B is provided on the surface of the electrode portion 12, even if the device is repeatedly used for treatment of the living tissue, the living tissue does not adhere easily and the electrical conductivity can be maintained in good condition. Therefore, the high-frequency device 10B has excellent durability.

In particular, in the second modified example, since each of the large-diameter filler 5A and the small-diameter filler 5B has an elongated shape with corners, even if the amount of the fillers 5A and 5B is small, the fillers 5A and 5B are easily fused to each other, and the conductive paths can be formed more reliably. That is, by setting the addition amount of the large-diameter filler 5A to, for example, about 50 wt % and the addition amount of the small-diameter filler 5B to, for example, about 10 wt %, the area of the large-diameter filler 5A exposed on the electrode surface 1*b* can be maintained small, and the interval between the exposed portions 5*b* of the large-diameter filler 5A can be prevented from becoming too narrow. As a result, on the electrode surface 1*b*, the surface area of the silicone resin 4 having high adhesion prevention property of the living tissue can be secured, and the adhesion prevention property of the living tissue on the electrode surface 1*b* can be maintained.

In the second modified example, since the average particle size of the small-diameter filler 5B is small, a large number of fused portions with the electrode substrate 1A are formed, and high adhesion with the electrode substrate 1A is obtained.

In addition, in the second modified example, the layer mainly containing the large-diameter filler 5A and the layer mainly containing the small-diameter filler 5A in the conductive adhesion preventing film 1B are formed of the same silicone resin 4, so that high adhesion can be obtained. That is, when only the small-diameter filler 5B is provided, it tends to concentrate in the vicinity of the electrode substrate 1A, and the adhesion to the electrode substrate 1A can be ensured, but the density on the electrode surface 1*b* side decreases. Therefore, the portion where the small-diameter fillers 5B are fused and combined to the electrode surface 1*b* side is reduced, and a sufficient conductive path cannot be formed. On the other hand, in the case of using only the large-diameter filler 5A as in the first modified example, sufficient adhesive strength may not be obtained due to the small number of junctions with the electrode substrate 1A. Therefore, by using fillers having two different particle diameters, the large-diameter filler 5A and the small-diameter filler 5B, as in the second modified example, it is possible to achieve both high adhesion and conductivity in a well-balanced manner.

Furthermore, by setting the average particle diameter of the small-diameter filler 5B to 1 μm or less, more preferably 0.5 μm or less, the fusion bonding area with the electrode substrate 1A can be increased. In addition, by setting the average particle size of the large-diameter filler 5A to be larger than 1 μm, preferably 4 μm or more, it is possible to efficiently form a conductive path even if the amount added in the silicone resin 4 is small. Thereby, it is possible to increase the ratio of the silicone resin for exhibiting the sticking prevention property.

In addition, when a layer is formed with a coating material containing only the small-diameter filler 5B and then a layer is formed with a coating material containing only the large-diameter filler 5A, it is possible to exhibit the same performance with a small addition amount, and the boundary of each layer becomes clear.

Furthermore, in the second modified example, when a solid and high-density small-diameter filler 5B is used, it settles after coating and tends to gather in the vicinity of the electrode substrate 1A. In addition, when a large-diameter filler 5A having a low density is used, it is difficult to settle after coating, and can be uniformly dispersed from the vicinity of the electrode substrate 1A to the electrode surface 1*b*, and a conductive path can be efficiently formed. In particular, hollow materials plated with metal have the lowest density and can be stably dispersed.

Third Modified Example

An electrode for a high-frequency medical device and a medical device according to a third modified example of the present embodiment will be described.

Figure 7:
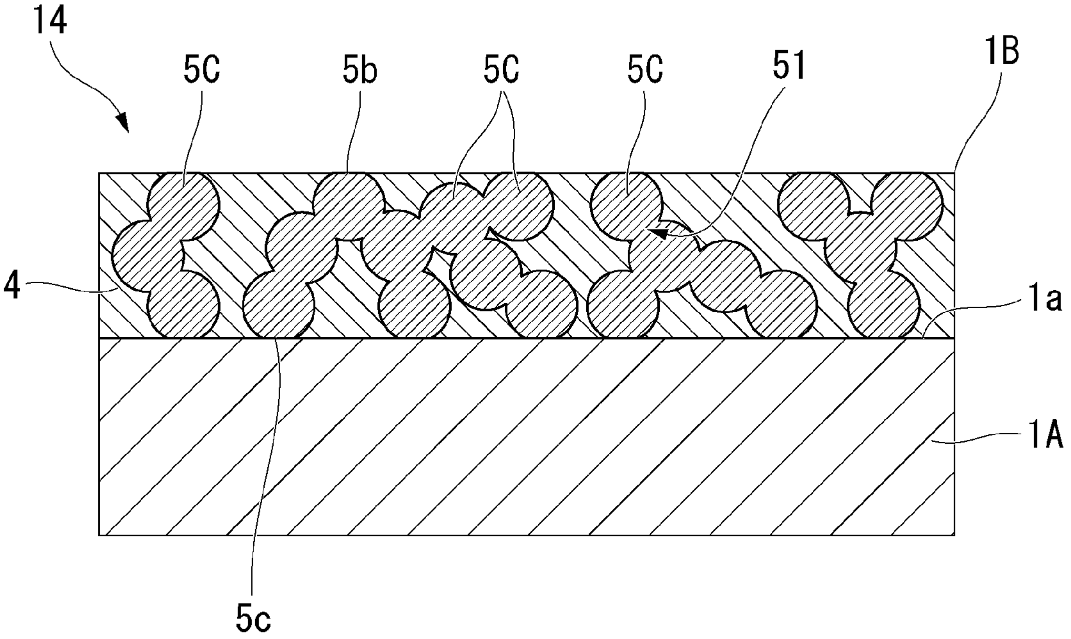
FIG. 7 is a schematic cross-sectional view of an electrode for a high-frequency medical device according to a third modified example of the embodiment of the present invention.

FIG. 7 is a schematic cross-sectional view of an electrode for a high-frequency medical device according to a third modified example of the embodiment of the present invention.

As shown in FIG. 1, a high-frequency device 10C (medical device) of the third modified example includes an electrode portion 14 instead of the electrode portion 1 in the above embodiment. As shown in FIGS. 2 and 7, the electrode portion 14 in the third modified example includes the conductive adhesion preventing film 1B (conductive adhesion preventing film for medical use) containing spherical filler 5C instead of the flake-shaped fillers 5 of the embodiment.

The following description will focus on points that differ from the above embodiment.

As schematically shown in FIG. 7, the filler 5C added to the silicone resin 4 of the conductive adhesion preventing film 1B is spherical. It is more preferable that the spherical filler 5C have an average particle size of 3 μm or more in the longitudinal direction and a true density of 11 g/cm 3 or less as in the above embodiment. Also, in the conductive adhesion preventing film 1B of the third modified example, at least one of particles of the filler 5C and the filler 5C and the electrode substrate 1A located on the surface of the treatment section is combined by thermal fusion.

Also, the amount of the filler 5C added according to the third modified example is preferably 70 wt %, for example. Furthermore, the average particle diameter of the filler 5C is preferably 7 μm or more.

The material of the filler 5C is the same as in the above embodiment, and may be metal. The electrical resistivity of the metal used for the filler 5C may be, for example, 952 or less. Examples of metals with low electrical resistivity include silver, nickel, copper, and gold.

According to the high-frequency device 10C according to the third modified example, since the conductive adhesion preventing film 1B is provided on the surface of the electrode portion 13, even if the device is repeatedly used for treatment of the living tissue, the living tissue does not adhere easily and the electrical conductivity can be maintained in good condition. Therefore, the high-frequency device 10C has excellent durability.

By setting the added amount of the filler 5C to, for example, about 70 wt %, the area of the filler 5C exposed on the electrode surface 1*b* can be reduced, and the gap between the exposed portions 5*b* of the filler 5C can be prevented from becoming too narrow. As a result, on the electrode surface 1*b*, the surface area of the silicone resin 4 having high adhesion prevention property of the living tissue can be secured, and the adhesion prevention property of the living tissue on the electrode surface 1*b* can be maintained.

Fourth Modified Example

A description will be given of the electrode for a high-frequency medical device and the medical device of the fourth modified example of the present embodiment.

Figure 8:
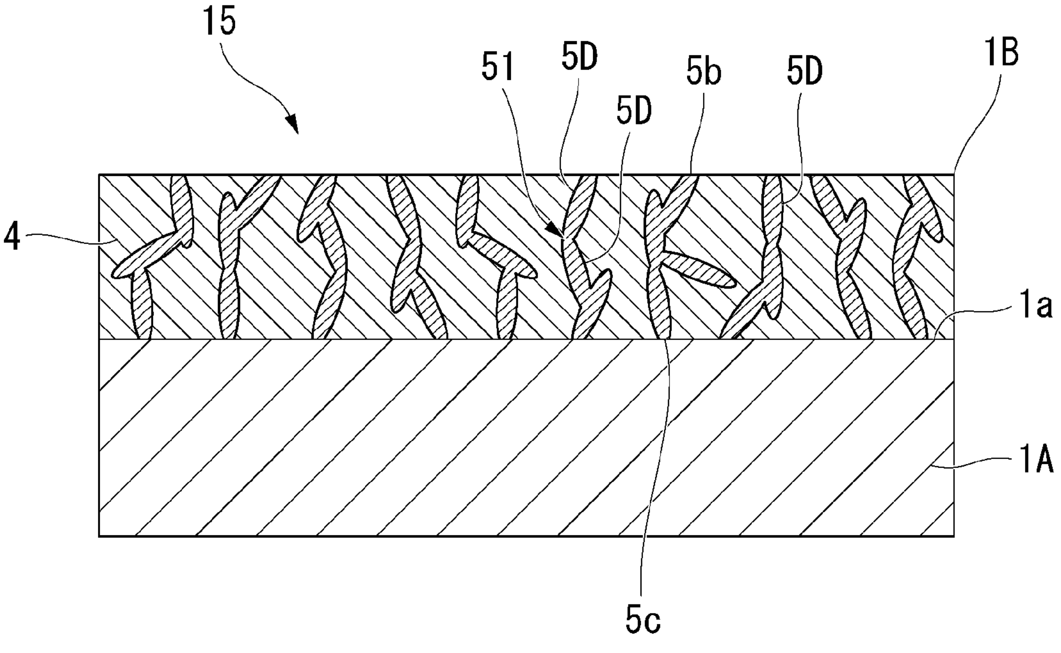
FIG. 8 is a schematic cross-sectional view of an electrode for a high-frequency medical device according to a fourth modified example of the embodiment of the present invention.

FIG. 8 is a schematic cross-sectional view of an electrode for a high-frequency medical device according to a fourth modified example of the embodiment of the present invention.

As shown in FIG. 1, a high-frequency device 10D (medical device) of the fourth modified example includes an electrode portion 15 instead of the electrode portion 11 of the first modified example. As shown in FIGS. 2 and 8, the electrode portion 15 in the fourth modified example includes the conductive adhesion preventing film 1B includes a spherical filler 5D (conductive adhesion preventing film for medical use) instead of the flake-shaped filler 5 of the embodiment.

The following description will focus on points that differ from the above embodiment.

As schematically shown in FIG. 8, the filler 5D added to the silicone resin 4 of the conductive adhesion preventing film 1B is formed in an elongated elliptical shape. As in the above embodiment, the filler 5D also preferably has an average particle diameter of 3 μm or more in the longitudinal direction and a true density of 11 g/cm 3 or less. Also, in the conductive adhesion preventing film 1B of the fourth modified example, at least one of particles of the filler 5D and the filler 5D and the electrode substrate 1A located on the surface of the treatment section is combined by thermal fusion.

Also, the amount of filler 5D added according to the fourth modified example is preferably 70 wt %, for example. Furthermore, the average particle size of the filler 5D is preferably 7 μm or more.

The material of the filler 5D is the same as in the above embodiment, and may be metal. The electrical resistivity of the metal used for the filler 5A may be, for example, 9Ω or less. Examples of metals with low electrical resistivity include silver, nickel, copper, and gold.

According to the high-frequency device 10D according to the fourth modified example, the conductive adhesion preventing film 1B is provided on the surface of the electrode portion 15. Therefore, even if the device is repeatedly used for treatment of the living tissue, the living tissue does not adhere easily and the electrical conductivity can be maintained in good condition. Therefore, the high-frequency device 10D has excellent durability.

By setting the amount of the filler 5D added to, for example, about 70 wt %, the area of the filler 5D exposed on the electrode surface 1*b* can be reduced, and the gap between the exposed portions 5*b* of the filler 5D can be prevented from becoming too narrow. As a result, on the electrode surface 1*b*, the surface area of the silicone resin 4 having high adhesion prevention property of the living tissue can be secured, and the adhesion prevention property of the living tissue on the electrode surface 1*b* can be maintained.

First Embodiment

Next, Examples 1 to 5 of electrodes for high-frequency medical devices corresponding to the above-described embodiment, first modified example, and second modified example will be described together with Comparative Examples 1 to 6. Table and Table 2 in FIGS. 10A and 10B, respectively, show schematic configurations and evaluation results of each example and comparative example.

A silicone resin was used as the material of the silicone resin 4 of the electrodes used in Examples 1 to 5 and Comparative Examples 1 to 6. In general, silicone resin is mainly composed of three-dimensional siloxane bonds (T units), and represents a hard film with a high crosslink density, and silicone rubber refers to a flexible film mainly composed of two-dimensional siloxane bonds (D units). The term "silicone resin" as used in this embodiment means a combination of a silicone resin and a silicone rubber, which means a silicone that has hardness enough to ensure scratch resistance and flexibility that can follow the thermal expansion and contraction of the base material. Specifically, SILRES (registered trademark) MPF52E (trade name; manufactured by Asahi Kasei Wacker Silicone Co., Ltd.) was used as the silicone resin in this embodiment.

As shown in Table 1 and Table 2, in the conductive fillers used in Examples 1 to and Comparative Examples 1 to 6 (abbreviated simply as "filler" in Table 1 and Table 2), there are cases where one type is used (Examples 1 to 4 and Comparative Examples 1 to 6) and cases where two types are used (Example 5). In the case of one type of filler, the material and properties of the filler described in "Filler (1)" in Table 1 and Table 2 were used. In the case of two types of fillers, filler materials and physical properties described in "Filler (1)" and "Filler (2)" in Table 1 and Table 2 were used.

In addition, in Table 1 and Table 2, the conductive fillers used in this example are commercially available specific types of "a", "b", "c", "d", and "e"., and "f", and conductive fillers other than those types are indicated by "-". Further, conductive fillers "a" to "f" are referred to as fillers a to f, respectively, and have the shapes and forms shown in the schematic diagrams of FIGS. 9A to 9F, respectively. Although FIG. 9G is not used in Examples 1 to 5 and Comparative Examples 1 to 6, it is shown as an adhesion reference.

The material and physical properties of the specific conductive fillers used in Examples 1 to 5 and Comparative Examples 1 to 6, addition amount (wt %), curing temperature (° C.), conductivity, adhesion, and evaluation method will be described below.

Example 1

Example 1 is an example of the electrode for a high-frequency medical device of the above embodiment.

As shown in Table 1, the filler (1) was obtained by adding a silver filler that has a flake shape with corners and curing at 150° C. or higher to melt the corners and fuse the fillers. Specifically, the filler was made of silver and had a flaky shape with corners, an average particle diameter of 2 μm, and a true density of 10.5 g/cm 3. The filler was dried under conditions of an addition amount of 90 wt % and a curing temperature of 150° C. to form a film.

Example 2

Example 2 is an example of the electrode for a high-frequency medical device of the above embodiment.

As shown in Table 1, the filler (1) was obtained by adding silver filler that has a flake shape with corners and curing at 150° C. or higher to melt the corners and fuse the fillers. Specifically, the filler was made of silver and had a flaky shape with corners, an average particle size of 3.5 μm, and a true density of 12.0 g/cm 3. The filler was dried under conditions of an addition amount of 90 wt % and a curing temperature of 150° C. to form a film.

Example 3

Example 3 is an example of the electrode for a high-frequency medical device of the above embodiment.

Figure 9A:
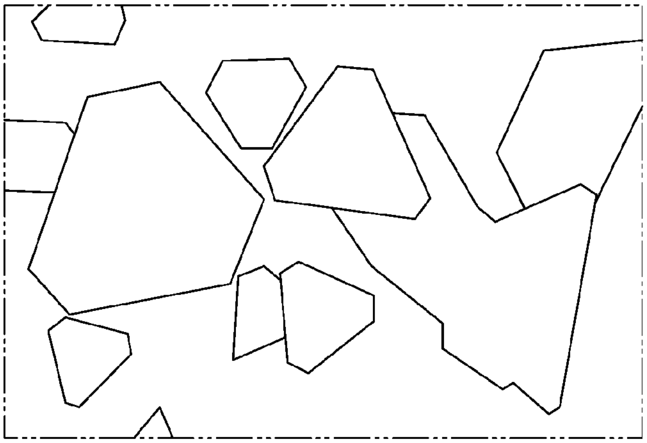
FIG. 9A is a diagram schematically showing a conductive filler according to an example.

As shown in Table 1, the filler (1) is filler a, a silver filler that has a flake shape with corners, and cures the filler at a curing temperature of 150° C., so that the corners are melted and the fillers are fused together (see FIG. 9A). Specifically, the filler a was made of silver and had a flaky shape with corners, an average particle size of 3.5 μm, and a true density of 10.5 g/cm 3. The amount of filler a added was 80 wt %, and the film was formed by drying under the temperature conditions of a curing temperature of 150° C.

Example 4

Example 4 is an example of the electrode for a high-frequency medical device of the above embodiment.

Figure 9B:
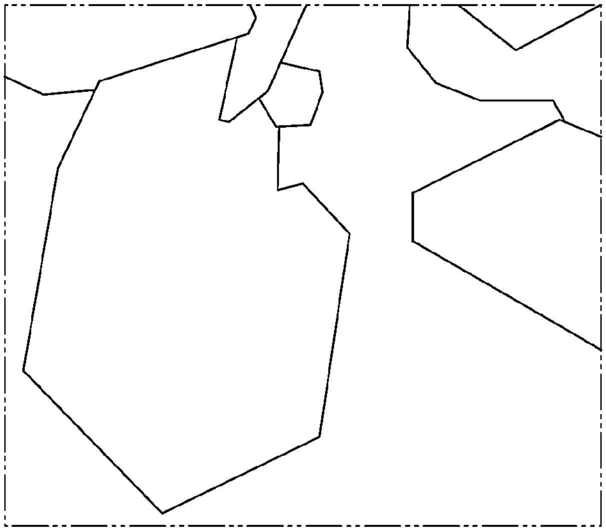
FIG. 9B is a diagram schematically showing a conductive filler according to an example.
Figure 9C:
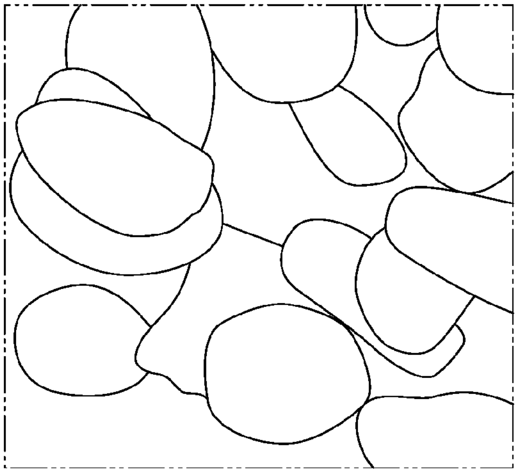
FIG. 9C is a diagram schematically showing a conductive filler according to a comparative example.
Figure 9D:
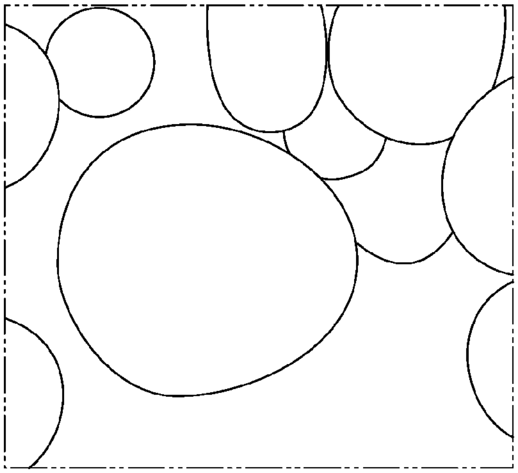
FIG. 9D is a diagram schematically showing a conductive filler according to a comparative example.
Figure 9E:
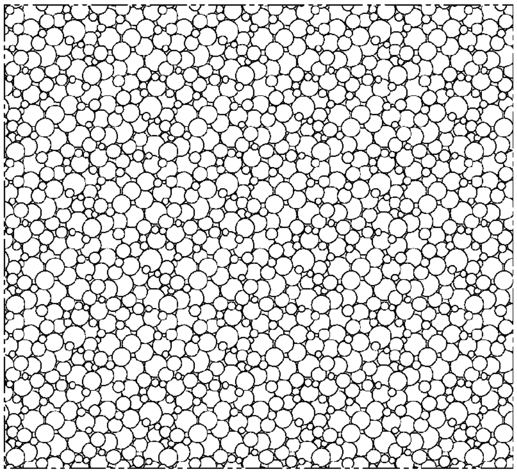
FIG. 9E is a diagram schematically showing a conductive filler according to a comparative example.
Figure 9F:
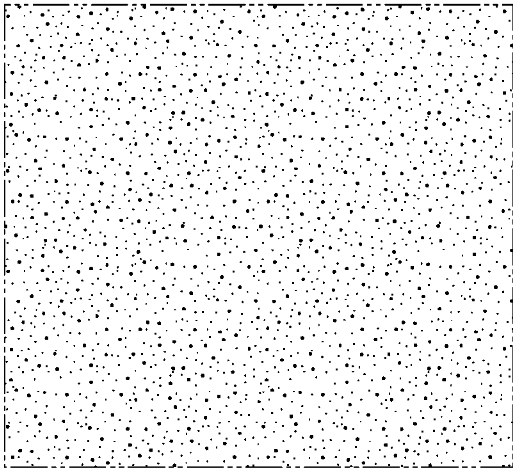
FIG. 9F is a diagram schematically showing a conductive filler according to a comparative example.
Figure 9G:
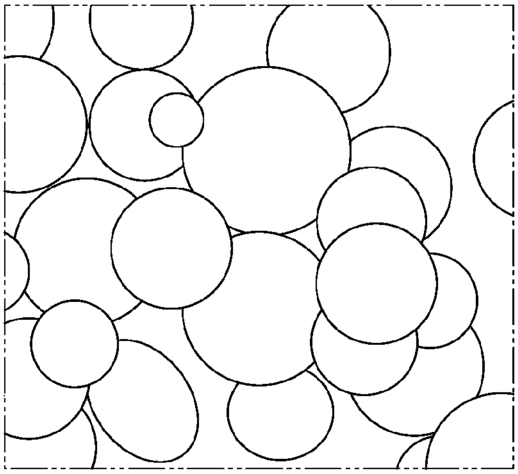
FIG. 9G is a diagram schematically showing a conductive filler according to a comparative example.

As shown in Table 1, the filler (1) is the filler b, has a flake shape with corners and is coated with a metal, and cures at a curing temperature of 200° C., so that the corners are melted and the fillers are fused together (see FIG. 9B). Specifically, the filler b was made of alumina coated with silver, and had a flaky shape with corners, an average particle diameter of 13 μm, and a true density of 5.8 g/cm 3. The amount of filler b added was 60 wt %, and the film was formed by drying under the conditions of a curing temperature of 200° C.

Example 5

Example 5 is an example of the electrode for a high-frequency medical device of the second modified example.

As shown in Table 1, two types of filler (1) with a large particle size and filler (2) with a small particle size are used. The filler (1) is filler a, and silver filler that has a flake shape with corners is added and cured at a curing temperature of 180° C., so that the corners are melted and the fillers are fused together. Specifically, the filler a was made of silver and had a flaky shape with corners, an average particle size of 3.5 μm, and a true density of 10.5 g/cm 3. The filler (2) is filler e, and silver filler having a smaller diameter and higher density than filler a is added, and the filler is melted at a curing temperature of 180° C. to fuse the fillers (See FIG. 9E). Specifically, the filler e was made of silver, had an average particle size of 0.8 μm, and had a true density of 10.5 g/cm 3. The fillers a and e were added in amounts of 50 wt % and 10 wt %, respectively, and both were dried at a curing temperature of 180° C. to form a film. In Example 5, a filler e having a small particle size and high density was added to Example 1 described above, so that the filler e, which is small and has high density, was concentrated in the vicinity of the electrode substrate.

Comparative Examples 1 to 6

Comparative Examples 1 to 6 will be described, focusing on the differences from Examples 1 to 5 above.

As shown in Table 2, Comparative Examples 1 and 2 employ the same filler a as in Example 3. The difference between Comparative Example 1 and Example 3 is that the curing temperature was set to 140° C. Comparative Example 1 was deposited at a curing temperature 10° C. lower than Example 3, which had a curing temperature of 150° C. The difference between Comparative Example 2 and Example 3 is that the amount added was 95 wt % and the curing temperature was 140° C. In Comparative Example 2, the amount added was 80 wt %. In addition, the film was formed at a curing temperature lower by 10° C. than in Example 3, in which the curing temperature was 150° C.

In Comparative Example 3, as shown in Table 2, the filler c was used, and the filler was added and cured at a curing temperature of 200° C. (See FIG. 9C). Specifically, the filler c was made of a silver-coated body, was in the form of flakes with no corners, had an average particle size of 6.5 μm, and had a true density of 9.2 g/cm 3. The amount of filler c added was 88 wt %, and the film was formed by drying under the conditions of a curing temperature of 200° C. The filler of Comparative Example 3 differs from Examples 1 to 5 in that it has a flaky shape without corners.

In Comparative Example 4, as shown in Table 2, the filler d was used, a spherical metal-coated filler was added, and the filler was cured at a curing temperature of 200° C. (See FIG. 9D). Specifically, the filler d is made of silver-coated aluminum, has a spherical shape, and has an average particle size of 7.0 μm and a true density of 3.5 g/cm 3. The amount of filler d added was 73 wt %, and the film was formed by drying under the conditions of a curing temperature of 200° C. The filler of Comparative Example 3 differs from Examples 1 to 5 in that it is spherical rather than flaky.

In Comparative Example 5, as shown in Table 2, a filler e was used, and a silver filler having a smaller diameter and a higher density than the other fillers a, b, c, and d was added and cured at a curing temperature of 150° C. (See FIG. 9E). Specifically, the filler e was made of silver, had an average particle size of 0.8 μm, and had a true density of 10.5 g/cm 3. The filler e was formed into a film by drying under temperature conditions of an addition amount of 96 wt % and a curing temperature of 150° C.

In Comparative Example 6, as shown in Table 2, a filler f was used, a filler made of carbon fine particles was added, and cured at a curing temperature of 150° C. (See FIG. 9F). Specifically, the filler f was fine particles made of carbon, had an average particle size of 0.04 μm, and had an unknown true density. The filler f was formed into a film by drying under temperature conditions of an addition amount of 17 wt % and a curing temperature of 150° C.

Here, FIG. 9G is a reference example of a filler that is not used in Examples 1-5 and Comparative Examples 1-6. The filler shown in FIG. 9G was made of silver and had a spherical shape with an average particle size of 3.9 μm and a true density of 10.5 g/cm 3. The filler is added in an amount of 96 wt %.

Evaluation Method

The test samples of Examples 1 to 5 and Comparative Examples 1 to 6 were subjected to conductivity evaluation and filler adhesion evaluation.

In the conductivity evaluation, the electrodes according to Examples (Examples to 5, Comparative Examples 1 to 6) are attached to the distal end of the device for sealing blood vessels. Then, the porcine blood vessel is gripped and pressed by the electrode portion, and a high frequency is applied while the blood vessel is occluded. If the blood vessel can be sealed, the conductivity is “good” (described as “A” in Table 1), and if the blood vessel can not be sealed, the conductivity is “bad” (described as “B” in Table 1).

In the filler adhesion evaluation and the adhesion prevention evaluation, the number of times blood vessels can be sealed in the above conductivity evaluation is counted. That is, the number of times blood vessels are sealed when the fillers are peeled off from each other or when the filler and the electrode substrate are peeled off is counted, and the number of blood vessel sealing times is referred to as the possible number of blood vessel sealings. If the number of times the vessel can be sealed is 5 or less, the adhesion property (described as "adhesion" in Tables 1 and 2) is defined as "bad" (the number of times is described together with "B" in Tables 1 and 2), and If the number of times the vessel can be sealed is 30 or more, the adhesion property is defined as "good" (the number of times is described together with "A" in Tables 1 and 2). Furthermore, those with particularly good adhesion of 60 times or more, which is optimal for a device for sealing blood vessels that can be sealed a large number of times per procedure, are labeled as "AA" in Table 1 and Table 2.

Evaluation Results

As shown in Table 1, Examples 1 to 5 were "good" with "A" or "AA" in both the conductivity evaluation and the filler adhesion evaluation. In Examples 1 to 5, sufficient conductivity can be obtained, and it can be confirmed that the filler is melted and fused with the base material, so it is considered that sufficient durability can be obtained.

In Example 3, the flaky silver filler having corners (filler a) has an average particle diameter of 3 μm or more and a true density of 11 g/cm or less, so that it becomes difficult to sink and is easily dispersed uniformly in the silicone resin. It was found that good electrical conductivity can be obtained even with an addition amount of 80 wt %, which is smaller than that in Examples 1 and 2.

In Example 4, by using a filler (filler b) in which a filler having corners is used as a core and coated with alumina metal (filler b), the cost can be reduced compared to the case where silver is used as in Examples 1 to 3. It was also found that the use of a core having a small specific gravity such as alumina or silica as in the fourth embodiment makes it difficult for the filler to sink, and furthermore, it is possible to obtain electrical conductivity with a small amount.

In Example 5, in addition to the filler a of Example 1, the filler e having a small particle size and high density is mixed, so that the base material and the filler are fused together by curing at a high temperature, and it is considered that high adhesion strength can be obtained.

On the other hand, in Comparative Examples 1 to 6, at least one of the conductivity evaluation and the filler adhesion evaluation was "bad". In the conductivity evaluation, Comparative Examples 1 and 6 are "B" and "bad". In the evaluation of filler adhesion, Comparative Examples 2 to 6 were "B" and "bad", and Comparative Example 1 could not be evaluated.

the amount of added filler, the contact points between the fillers can be increased and the conductivity can be obtained. It can be confirmed that adhesion does not occur, and furthermore, it is considered that adhesion between the silicone resin and the electrode substrate is deteriorated, so it is understood that sufficient adhesion cannot be obtained.

Compared to Examples 1 to 5, Comparative Example 3 is a flake-shaped filler (filler c) that does not have corners, so it can be confirmed that the fillers do not fuse together due to melting of the corners. In order to ensure conductivity, a large amount of filler must be added, but in that case, adhesion between the electrode substrate and the silicone resin is hindered and sufficient adhesion cannot be obtained.

Compared to Examples 1 to 5, Comparative Example 4 is a spherical filler (filler d) that does not have corners, so similarly to Comparative Example 3, it can be confirmed that fusion of fillers due to melting of corners does not occur. In order to ensure conductivity, a large amount of filler must be added, but in that case, adhesion between the electrode substrate and the silicone resin is hindered and sufficient adhesion cannot be obtained.

Compared to Examples 1 to 5, Comparative Example 5 uses a filler (filler e) having a smaller average particle size, so the amount of filler to be added must be increased in order to form a conductive path. In that case, adhesion between the electrode substrate and the silicone resin is hindered, and sufficient adhesion cannot be obtained.

In Comparative Example 6, compared to Examples 1 to 5, the filler made of carbon (filler f) has an extremely small average particle size, so even if a large amount of filler is added, sufficient conductivity cannot be obtained. In addition, although the weight ratio is small, the density is small, so the volume ratio is extremely large, and adhesion cannot be obtained.

Second Embodiment

Next, Examples 1 and 2 of electrodes for high-frequency medical devices corresponding to the above-described embodiment, first modified example, and second modified example in the second example will be described along with comparative examples 1 to 3. Table 3 below shows the schematic configuration and evaluation results of each example and comparative example.

In the second example, an adhesion prevention evaluation was performed to evaluate the adhesion prevention property of living tissue in repeated use of electrodes for high-frequency medical device.

TABLE 3

| | Item | Comparative Example 1 | Comparative Example 2 | Comparative Example 3 | Example 1 | Example 2 |
|---|---|---|---|---|---|---|
| Particle | A[μm] | 3 | 0.5 | 1 | 1 | 1 |
| size | B[μm] | 2 | 1 | 4 | 4 | 4.5 |
| Baking | Temperature[° C.] | 160 | 200 | 80 | 160 | 260 |
| condition | Time[h] | 3 | 0.5 | 1 | 0.5 | 3 |
| Evaluation | Sticking rate(%) | 80 | 45 | 60 | 15 | 0 |
| | Result | B | B | B | A | A |

In Comparative Example 1, since the curing temperature was as low as 140° C. compared to Examples 1 to 5, fusion between fillers did not occur. As a result, it can be confirmed that sufficient conductivity cannot be obtained.

In Comparative Example 2, as compared with Examples 1 to 5, even if the curing temperature is low, by increasing As shown in Table 3, in Example 1, a filler a having a particle size of 1 μm and a filler b having a particle size of 4.5 μm were added to a silicone resin and a solvent and applied to the electrode substrate. After the application, it was allowed to stand still for 30 minutes, and then baked at a baking temperature of 260° C. for a baking time of 3 hours.

In Example 2, a filler a having a particle size of 1 μm and a filler b having a particle size of 4.0 μm were added to a silicone resin and a solvent and applied to the electrode substrate. After the application, it was allowed to stand for 30 minutes, and then baked at a baking temperature of 160° C. for a baking time of 0.5 hours (30 minutes).

The filler with a small medium particle size in Examples 1 and 2 sedimented after standing still for 30 minutes and was intensively distributed in the vicinity of the electrode substrate. The filler heated at 260° C. melts at the both ends, forming fusion bonds between the filler and the substrate and between the fillers.

As shown in Table 3, Comparative Examples 1 to 3 were prepared by changing the particle size of the filler, baking temperature (° C.), and baking time (H) from Examples 1 and 2. The standing time after application is 30 minutes as in the examples. [Evaluation method]

In the adhesion prevention evaluation according to the second example, a caul fat is immersed in a mixture of blood and physiological saline. Then, the caul fat is taken out, and the vessel of it is sealed 50 times using the same blood vessel sealing device as in the first embodiment. That is, as shown in Table 3, the caul is gripped and pressed by the electrodes, and a high frequency is applied. For the evaluation, the number of times the caul adhered/50 times×100 was taken as the sticking rate (%), those with a sticking rate of less than 30% were evaluated as "passed" (described as "A" in Table 3), and those with a sticking rate of 30% or more were evaluated as "failed" (described as "B" in Table 3).

Evaluation Results

As shown in Table 3, in Example 1, the sticking rate was 15%, and in Example 2, the sticking rate was 0%. Both were less than 30%, and the adhesion prevention evaluation was "A", which was "passed". In particular, in Example 2, during the 50 times, the caul never adhered.

On the other hand, in Comparative Examples 1 to 3, the sticking rate was 30% or more, and the adhesion prevention property evaluation was "B", which was "failed".

Although preferred embodiments and modified examples of the present invention have been described along with examples, the present invention is not limited to these embodiments, modified examples, and examples. Configuration additions, omissions, substitutions, and other changes are possible without departing from the scope of the present invention.

Also, the present invention is not limited by the above description, but only by the scope of the attached claims.

For example, in the description of the above embodiment and each modified example, the medical device provided with the medical conductive adhesion preventing film is a high-frequency device, but the medical device is not limited to a high-frequency device. Examples of other medical devices in which the medical conductive adhesion preventing film of the present invention can be suitably used include electric scalpels, high-frequency devices, bipolar tweezers, probes, treatment tools such as snares, and the like.

In addition, in the description of the above-described embodiment and each modified example, an example in which the medical conductive adhesion preventing film is laminated directly on the electrode substrate 1A has been described. A conductive single-layer or multi-layer intermediate layer may be interposed between the adhesion preventing film. As the intermediate layer, an appropriate conductive layer that improves the bonding strength between the electrode substrate 1A and the medical conductive adhesion preventing film may be used.

The present invention can be used for an electrode for a high-frequency medical device and a medical device.

What is claimed is:

1. An electrode for a high-frequency medical device, the electrode comprising:
- a treatment section; and
- a coating film formed on at least a part of a surface of the treatment section, wherein the coating film comprises:
  - a silicone resin, and
  - at least one type of filler having conductivity,
- wherein:
  - particles of the filler are fusion-bonded to each other to form a conductive path, and
  - the particles of the filler and an electrode substrate disposed on a surface of the treatment section are fusion-bonded to form a conductive path;
- wherein the particles have a shape with corners and the corners are bonded together by the fusion-bonding.

2. The electrode for the high-frequency medical device according to claim 1, wherein the filler has an average particle diameter of 3 μm or more, which is smaller than a thickness of the coating film, and has a true density of 11 $g/cm^3$ or less.

3. The electrode for the high-frequency medical device according to claim 1, wherein, in the filler, a core comprises aluminum, copper, a ceramic, alumina, silica, glass, calcium titanate fiber, a resin, acryl, hollow particles, rubber and an entire core coated with silver.

4. The electrode for the high-frequency medical device according to claim 1,
- wherein the filler comprises first filler with first particle size and second filler with second particle size,
- the first particle size is smaller than the second particle size and
- in a vicinity of the electrode base, a filler ratio with the first filler is higher than a filler ratio of the second filler.

5. A medical device comprising the electrode for the high-frequency medical device according to claim 1.

6. An electrode for a high-frequency medical device comprising:
- a treatment section; and
- a coating film formed on at least a portion of a surface of the treatment section, wherein the coating film is a conductive anti-adhesion film, the coating comprises:
  - a silicone resin; and
  - a conductive filler comprising a plurality of conductive particles,
- wherein the plurality of conductive particles are fusion-bonded to each other, or to the conductive filler and an electrode substrate located on the surface of the treatment section, to form a conductive path,
- an electrode surface of the coating film has an exposed portion where the conductive filler is exposed from the silicone resin, and a smooth surface of the silicone resin excluding the exposed portion,
- an area of the exposed portion in a plan view is smaller than a surface area of the silicone resin,
- the conductive filler comprises two or more particles with different particle sizes, and
- a proportion of the conductive filler with smaller particle sizes is higher near the electrode substrate.

* * * * *